US005558996A

United States Patent [19]
Bartlett et al.

[11] Patent Number: 5,558,996
[45] Date of Patent: Sep. 24, 1996

[54] FUNGUS EXTRACTION METHOD, KIT, AND EXTRACTION SOLUTION

[75] Inventors: William C. Bartlett, Wilmington; James M. Melby, Newark, both of Del.

[73] Assignee: Strategic Diagnostics Inc., Wilmington, Del.

[21] Appl. No.: 270,146

[22] Filed: Jul. 1, 1994

[51] Int. Cl.$^6$ .................................................... G01N 33/53

[52] U.S. Cl. ................. 435/7.31; 435/173.1; 435/173.7; 435/243; 435/254.1; 435/803; 435/810; 435/961; 435/962; 435/975; 436/174; 436/175; 436/177; 436/178; 436/825; 436/826; 510/199

[58] Field of Search ................................ 422/50, 61, 101; 435/7.1, 7.2, 7.31, 173.1, 173.4, 173.7, 243, 254.1, 803, 810, 820, 961, 962, 975; 436/174, 175, 177, 178, 825, 826; 540/145; 252/142, 174.21

[56] References Cited

U.S. PATENT DOCUMENTS

| | | | |
|---|---|---|---|
| 4,309,299 | 1/1982 | Rapisarda et al. | 252/95 |
| 4,650,754 | 3/1987 | Brambl . | |
| 4,693,968 | 9/1987 | Kitagawa | 435/7 |
| 4,851,337 | 7/1989 | Berke | 435/29 |
| 5,186,946 | 2/1993 | Vallieres | 424/613 |

FOREIGN PATENT DOCUMENTS

| | | |
|---|---|---|
| 0135378 | 3/1985 | European Pat. Off. . |
| WO91/02590 | 3/1991 | WIPO . |

OTHER PUBLICATIONS

*Chemical Abstracts*, vol. 118, No. 9, p. 638, col. 1, abstract No. 78951; Xia, J. Q. et al., "Monoclonal antibodies to an extracellular component of *Pyricularia grisea,*" *Can. J. Bot.*, 70(9):1790–1797 (1992).

*Chemical Abstracts*, vol. 108, No. 19, p. 380, col. 2, abstract 164630; Kitagawa, t. et al., "A novel enzyme immunoassay commonly applies for ten strains of *Pyricularia oryzae,*" *Microbiol. Immunol.*, 31(12):1197–1207 (1987).

Xia, J. O., et al., "Development of Monoclonal Antibodies Specific for *Pyricularia grisea,* the Rice Blast Pathogen," *Mycol. Res.*, 96:867–873 (1992).

C. Merodio et al, "Improved Separation of Green and Soluble Leaf Proteins by pH Shift", Journal of Agricultural Food Chemistry 31(5):956–959, 1983.

*Primary Examiner*—James C. Housel
*Assistant Examiner*—Christopher L. Chin
*Attorney, Agent, or Firm*—Jones & Askew

[57] ABSTRACT

A method and kit for extracting fungus from a plant. An extraction solution is combined with tissue from a plant and the combination is agitated, preferably by shaking, to extract a detectable amount of the fungus from the plant. The extraction solution is a solution containing a dilute acid and a detergent. The extract can then be neutralized without degradation of the fungus and subjected to analysis by immunoassay to detect the presence of pathogenic fungi. The method is particularly useful for the detection of *Pyricularia oryzae* on rice plants.

17 Claims, 1 Drawing Sheet

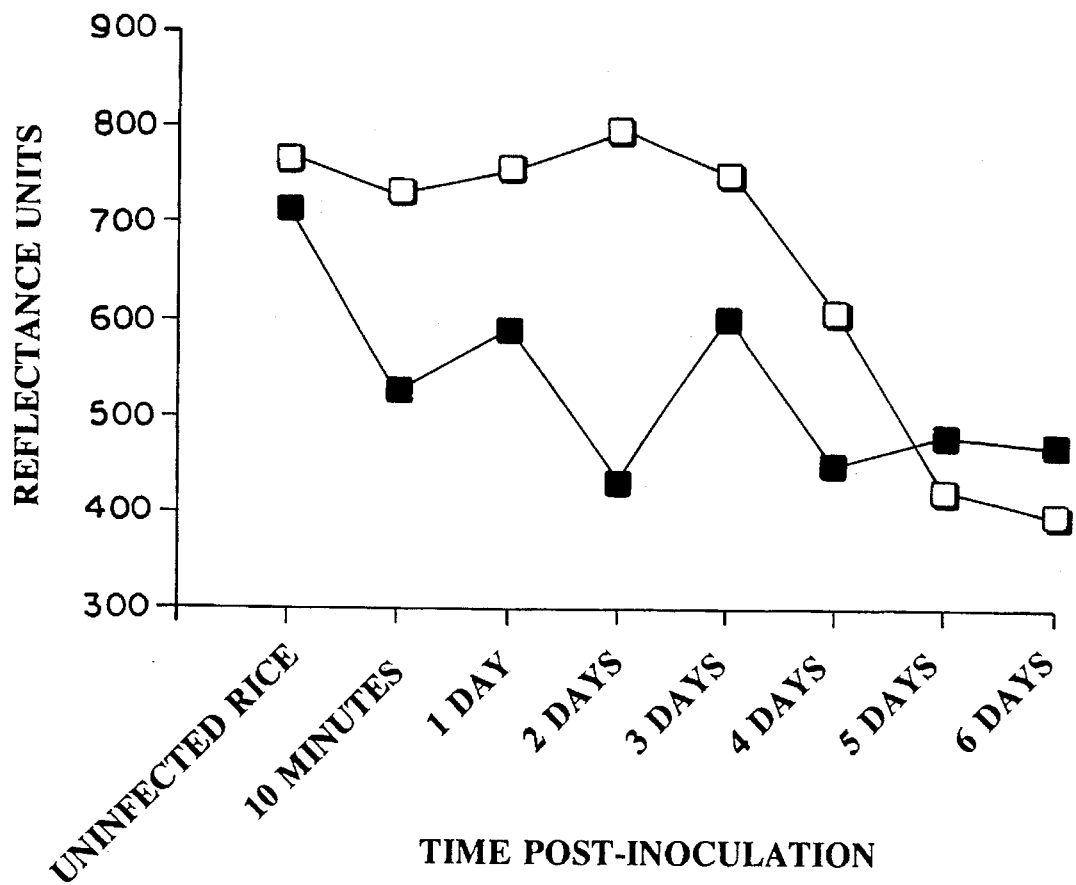
FIG_1

FUNGUS EXTRACTION METHOD, KIT, AND EXTRACTION SOLUTION

BACKGROUND OF THE INVENTION

This relates to the fields of chemistry and microbiology, and more particularly relates to chemical extraction of fungus from a plant.

Agricultural crops and ornamental plants are often plagued by parasites such as fungi. In particular, rice crops are highly susceptible to infection by the fungus *Pyricularia oryzae* (rice blast, also known as *Pyricularia grisea*).

Fungal infections of plants spread quickly from one area to another and, if not treated, will destroy entire crops. Numerous anti-fungus treatments are available. However, treatment must be commenced shortly after infection for the optimal effect and crop salvage.

Farmers often have difficulty detecting or identifying fungal disease until days or weeks after the onset of infection, allowing the fungus to become established and much more difficult to eradicate, resulting in the destruction of all or a large portion of the entire crop before the treatment takes effect. Therefore, rapid detection of a fungus infection is essential for effective treatment and ultimate crop survival.

A current method for the detection of the fungal infection of wheat known as Septoria or "cereal eyespot" involves grinding the wheat in the presence of a buffer to remove any fungus that may have been growing on the wheat, and testing the resulting buffer for the presence of fungus with an immunoassay. The major disadvantages to this method are that the grinding procedure is labor intensive, time consuming, expensive, and requires specialized machinery or equipment, and the buffer (following grinding) contains chlorophyll that could interfere with the immunoassay.

Farmers frequently administer anti-fungal treatment prophylactically, without conducting a test for the presence of fungal organisms because they are concerned that they will be unable to detect a fungal infection soon enough after infection to administer effective treatment.

Costly fungicides are therefore being liberally administered when there is a mere suspicion of a pathogenic fungal infection. This unwarranted administration of potentially toxic chemicals causes a threat to the consumer and the environment and greatly increases production costs.

Therefore, it is an object of the present invention to provide a rapid, sensitive method for the detection of a plant fungus infection.

It is a further object of the present invention to provide a kit for the detection of a fungus infection of a plant.

It is a further object of the present invention to provide a method for extracting fungus from plant tissue that is simple, rapid, and cost-efficient.

It is a further object of the present invention to provide an extraction solution for extracting fungus from plants.

SUMMARY OF THE INVENTION

A method and kit for extracting fungus from a plant is provided. In accordance with the method, an extraction solution is combined with tissue from a plant and the combination is agitated, preferably by shaking, to extract a detectable amount of the fungus from the plant. The extraction solution is a solution containing a dilute acid and a detergent. This solution reduces the amount of green color due to chlorophyll in the extract, thereby minimizing the amount of green pigment in the extract that could interfere with the immunoassay. In addition, the extraction solution is easily neutralized and does not degrade the fungus below a detectable level.

The extract can then be neutralized and subjected to analysis by immunoassay to detect the presence of pathogenic fungi.

The kit provided herein for the extraction of fungus from a plant sample contains a dilute acid and a detergent, which may be combined in the kit as a single extraction solution. The kit may additionally contain a reaction vessel in which the plant is reacted with the extraction solution and reagents for detection of the extracted fungus.

The extraction method and kit are preferably used in combination with an immunoassay to detect a fungus infection on a plant.

The method is particularly useful for the detection of *Pyricularia oryzae* on rice plants.

BRIEF DESCRIPTION OF THE DRAWINGS

FIG. 1 is a graph showing reflectance units versus time after inoculation with rice blast fungus. Reflectance units are inversely proportional to the amount of rice blast fungi present. The open square symbol represents reflectance in which the fungus was extracted from rice leaves by shaking with a solution containing a dilute acid and a surfactant in accordance with the method described herein. The closed square symbol represents grinding the leaves with a mortar and pestle in the presence of a neutral buffer.

DETAILED DESCRIPTION OF THE INVENTION

A plant fungus extraction method and kit are described. Plant tissue is combined with an extraction solution containing a dilute acid and a detergent and the combination is agitated for a sufficient amount of time to extract a sufficient amount of fungus from the plant tissue. The preferred agitation method is shaking. The extract, containing the fungus, may then be separated from the plant tissue and used for research, pharmaceutical, or diagnostic purposes or to monitor the effectiveness of an anti-fungal agent that has been applied to the plant. Preferably, the extraction method is combined with a detection method, such as an immunoassay for the detection of a plant fungal infection. Immunoassays for the detection of fungi are commercially available. The immunoassay can be qualitative or quantitative.

The method and kit are particularly useful in the field for diagnosis of a fungus infection. Treatment can then be immediately prescribed and the assay repeated any number of times to monitor the success of the treatment.

The method can be used to detect fungal growth shortly after the onset of infection providing that a detectable level of fungus is established on the plant tissue. Factors affecting the ability to detect infection include spore concentration, degree of susceptibility of the plant, and weather conditions. Less fungal growth occurs in dry weather. Under normal conditions, the method can often be used to detect fungal growth as soon as four days after infection, thereby allowing prompt commencement of treatment.

The extraction method is useful for extracting fungus growing on plants such as, but not limited to, grasses, trees, shrubs, flowers, and ornamental plants and is especially useful for extracting fungus growing on grasses such as rice, wheat, barley, rye, corn, and bananas.

All types of fungi should be able to be extracted by the described method. In addition, other pathogenic organisms such as bacteria and viruses of plants may also be extracted using this method. For example, the method is particularly useful for extracting Basidiomycetes, which include wheat rust, white pine blister rust, cedar apple rust, and smuts of corn, oats, barley, onions and wheat; Phycomycetes, which include downy mildew of grape and other hosts, root rot, and late blight of potato and tomato; and Ascomycetes, which include powdery mildew on cereal, fruits and many other crops, dutch elm disease, ergot of grains, peach and plum brown rot, block spot of roses, and apple scab. In addition, the extraction method is useful for extracting rice blast (*Pyricularia oryzae, Pyricularia grisea*), brown leaf spot (*Cochliobolus mizabeanus*), rice scald (*Rhynchosporium oryzae*), sheath blight (*Rhizoctonia solani*), bacterial blight/ streak (*Xanthomonas campestris*), and rice tungro virus (in which the vector is Green Leaf Hopper) from rice plants; powdery mildew (*Erysiphe graminis*), rusts (*Puccinia spp.*), bunts (*Tilletia spp.*), smuts (*Ustilago spp.*), septoria leaf spot (*Septoria spp.*), and take-all (*Gaeumannomyces graminis*) from wheat plants; rusts, powdery mildew, smuts, leaf blotch (*Rhynchosporium secalis*), net blotch (*Pyrenophora teres*), foot rot and ear blight (*Fusarium spp.*) from barley plants; rusts, smuts, stalk rots (*Fusarium spp.*), downy mildew (*Peronosclerospora spp.*), leaf blights (*Helminthosporium spp.*) and ear rot (*Gibberella sp., Fusarium sp.*) from corn; and grape storage rot (*Aspergillus niger*), grape powdery mildew (*Uncinula necator*), and grey mold (*Botrytis cinerea*) from grape plants.

The plant tissue from which the fungus is extracted is preferably a leaf, but may also be a flower, stem, seed, fruit, vegetable, root, or bark. The amount of material that should be subjected to extraction to obtain a detectable amount of fungus depends on the size of the plant tissue. For example, for a normal size rice leaf (¼ of an inch wide or less), approximately 30 inches of material is subjected to the extraction procedure for subsequent detection by immunoassay. For a wide rice leaf (¼ to ¾ inches wide), 15 inches of material will be sufficient for extraction and subsequent detection by immunoassay.

Extraction Solution

The extraction solution contains a dilute acid and a detergent. Any dilute acid may be used providing it does not degrade the fungus. For example, the dilute acid may be, but is not limited to, hydrochloric acid, sulfuric acid, acetic acid, nitric acid., and organic acids. Most preferably, the dilute acid is a 20 mM hydrochloric acid solution. This solution reduces the amount of green color due to chlorophyll in the extract, thereby minimizing the amount of green pigment in the extract that could interfere with the immunoassay.

The dilute acid is preferably diluted with water and is in the concentration range of between approximately 1 mM and 50 mM. At higher concentrations, the ability to neutralize the acid prior to detection by immunoassay, which is conducted at neutral pH, is adversely affected causing inferior results.

The detergent assists in washing the fungus off the surface of the plant tissue. The detergent may be ionic or non-ionic and includes, but is not limited to, an alkoxylated linear alcohol, a lauryl sulfate, a polyoxyethylene ester (such as a Triton™ surfactant, an MYRJ™ surfactant, and a Brij™ surfactant), a polyoxyethylenesorbitan (such as a Tween™ surfactant), a sorbitan (such as a Span™ surfactant), and a polyglycol ether surfactant (such as a Tergitol™) all available from either the Olin Corporation (Stamford, Conn.) or the Sigma Chemical Company (St. Louis, Mo.).

Other biological detergents that may be used are known to those skilled in the art. An exemplary list of biological detergents that may be used in the extraction solution described herein is given on pages 1645–1652 of the Sigma Catalog (Sigma, St. Louis, Mo.), which is incorporated herein by reference.

The preferred detergent is an alkoxylated linear alcohol. Most preferably, the detergent is the alkoxylated linear alcohol Poly-Tergent SLF-18™, a low foam surfactant commercially available from Olin Corporation (Stamford, Conn.). Poly-Tergent SLF™ surfactants having carbon chains of different lengths, such as SLF-45 and SLF-62 are also useful.

The detergent is preferably in a concentration range between approximately 0.01 and 1%, most preferably a concentration of approximately 0.1%. The preferred diluent is water.

Preferably, the extraction solution is premixed and is added to the plant tissue. It will be understood by those skilled in the art that the dilute acid and detergent could be added separately to the plant tissue. Approximately 2 ml of extraction solution is added to each 15 to 30 inches of plant tissue, depending on the width of the tissue, such as a leaf.

Agitation

Extraction of the fungus is accomplished by agitating the combination of plant tissue and extraction solution for a sufficient amount of time to extract a detectable amount of the fungus. Agitation is preferably achieved by shaking the mixture in a container, such as a plastic bottle. The container must be of a sufficient size to accommodate the plant tissue, the volume of extraction solution, and sufficient room for unimpeded agitation. Alternative agitation methods include, but are not limited to, stirring, vortexing, sonicating or vibrating, providing that the agitation method does not degrade the fungus.

Preferably, the plant tissue and extraction solution combination is agitated by moderate to vigorous shaking by hand. Agitation may be performed for any convenient length of time. Agitation for a length of time 30 minutes or less is preferred. The optimal length of time is approximately 3 minutes.

The agitation can be performed at any environmental temperature (approximately 65°–100° F.). The most preferred temperature is an environmental temperature at which the detergent is slightly insoluble. The preferred temperature for the Poly-Tergent SLF-18™ surfactant is 15° C. or higher.

Immunoassay

Prior to analysis of the extract by immunoassay for detection of fungus, the extract should be filtered to separate the extract containing the fungus from any large pieces of plant tissue that may interfere in the immunoassay. The preferred filter is a polyethylene filter having a pore diameter of approximately 1 μm. For optimal convenience, the filter is a filter tip, such as a filter tip available from Porex Technologies (Fairburn, Ga.) that can be attached to the opening of the container in which the extraction procedure takes place.

The filtered extract should be neutralized, or restored to a pH of between approximately pH 6 and pH 8 prior to analysis by immunoassay to obtain maximal sensitivity. Preferably, neutralization is achieved by the addition of a sufficient amount of a neutral pH buffer such as Hepes™ buffer or Trizma™ buffer. Neutral pH buffers are available commercially from chemical companies such as the Sigma Chemical Co. (St. Louis, Mo.) or can be prepared from salts in accordance with methods well known by those skilled in the art.

For detection, the neutralized extract is reacted with an antibody specific for the fungus being detected, and the antibody-antigen complex is detected in accordance with methods well known to those skilled in the art. The antibody specific for the fungus to be detected can be either polyclonal or monoclonal.

Antibodies are typically generated by immunizing an animal with an immunogenic amount of the antigen emulsified in an adjuvant such as Freund's complete adjuvant, administered over a period of weeks in two to three week intervals, (preferably the first immunization in Freund's complete adjuvant and subsequent immunizations in Freund's incomplete adjuvant at biweekly to monthly intervals thereafter) then isolating the antibodies from the serum, or fusing spleen cells to myeloma cells to make hybridomas which express the antibodies in culture. Test bleeds are preferably taken at fourteen day intervals between the second and third immunizations and production bleeds at monthly intervals thereafter.

For example, both polyclonal or monoclonal antibodies specific for the fungi to be detected can be prepared as described by Xia, J. Q. et al., "Development of monoclonal antibodies specific for *Pyricularia grisea*, the rice blast pathogen", *Mycol. Res.* 96:867–873 (1992), which is incorporated by reference herein. In the preferred embodiment of the present detection method, the method of Xia et al. is modified by preparing antigen either with soluble fractions obtained by centrifugation of crushed sporulating hyphae of *P. grisea* fungus or with frozen *P. grisea* mycelia, frozen in liquid nitrogen, crushed in a mortar and pestle, suspended in phosphate buffered saline and sonicated.

The antibody can be immobilized on a solid phase to facilitate detection. It will be understood by those skilled in the art that the solid phase can be latex, polystyrene, polyethylene, polypropylene, polycarbonate or any solid plastic material in the shape of test tubes, beads, microparticles, dip-sticks or the like. A solid phase also includes glass beads, glass test tubes and any other appropriate shape made of glass. Preferably, the solid phase is a latex bead.

Preferred detection methods include a direct or indirect enzyme-linked immunosorbent assay (ELISA) using a secondary antibody such as a peroxidase-conjugated goat anti-mouse antibody or a direct or indirect immunofluorescence assay using a secondary antibody such as a fluorescein isothiocyanate (FITC)-conjugated goat anti-mouse antibody.

The most preferred immunoassay detection method employs an enzyme-conjugated polyclonal antibody specific for the fungus to be detected, containing an enzyme that is reactive with a substrate to produce a detectable color. The reaction is stopped by the addition of a stop solution, which may contain a preservative to preserve the color for several hours until the results are read on a spectrophotometer, reflectometer or compared with a color chart.

Fungus Extraction and Detection Kit

The fungus extraction kit contains a dilute acid and a detergent, which may be combined in the kit as a single extraction solution. The kit may additionally contain a reaction vessel in which the plant is reacted with the extraction solution, a reference sample, a filtering device, an anti-fungus antibody-coated solid phase, a detectable anti-fungus antibody conjugate, reagents for neutralization and detection of the extracted fungus, and containers in which the sample and reagents may be incubated and reactants washed.

The reaction vessel is preferably an inert bottle, such as a plastic bottle, containing a sufficient amount of the extraction solution to extract a detectable amount of fungus. The filtering device is used for removing pieces of plant tissue from the extract that might interfere with detection. Preferably, the filtering device is a commercially available filter tip having a pore size of approximately 0.2 μm to 2 μm, most preferably 1 μm, (Porex Technologies, Fairburn, Ga.) that can be attached to the opening of the reaction vessel.

The kit may also contain a reference sample of the fungal antigen to be detected so that a color comparison may be made directly in the field. The reference sample may be lyophilized and a resuspension buffer included for reconstitution of the fungal antigen. Preferably, the reconstitution buffer is the extraction solution.

The antibodies are preferably polyclonal antibodies prepared in accordance with methods well known to those skilled in the art as described above and are specific for an antigen of the fungus to be detected. Monoclonal antibodies may also be used. Two preparations of the anti-fungal antibody should be provided with the kit. A first antibody preparation is preferably an antibody coated onto a solid phase, such as a latex bead and a second antibody preparation is preferably an enzyme conjugated antibody.

Vials may be included with the kit to conveniently hold the plant tissue extract and reference sample during incubation with the detection reagents. These vials preferably contain lyophilized immunoreagents in a neutralization buffer. Preferably, the vial is a transparent vessel.

A cup assembly may be included with the kit to allow for separation of the reacted from the unreacted immunoreagents. The cup assembly preferably has two adjacent compartments for visualization of a colorimetric change.

Reagents that may be included with the kit include a neutralization buffer for neutralizing the extract prior to immunoassay, a wash buffer to separate the reacted from the unreacted immunoreagents, a substrate or substrate buffer that reacts with the enzyme of the enzyme-conjugated antibodies, and a stop solution with preservatives that preserve the color of the reaction. The neutralization buffer is a buffer having a pH between 6 and 9 such a Hepes buffer containing 0.5M EDTA, 0.2% IgG, 0.05% BSA and 0.05% sodium azide, and the wash buffer is a neutral buffer such as 10 mM Tris, pH 8.0, 0.1% SLF-18™ detergent, and 0.05% sodium azide. The preferred substrate buffer contains a substrate such as 5-bromo-4-chloro-3-indolyl phosphate in 2-amino-2-methyl-1-propanol buffer with magnesium ions (BCIP, Sigma Chemical Co., St. Louis, Mo.). The preferred stop solution contains buffer and preservative such as 36 mM sodium phosphate buffer containing 15 mM sodium azide.

The kit may additionally contain a color card for an immediate comparison of the reference sample to the plant tissue sample for a diagnosis of fungal infection in the field.

The fungus extraction method and kit will be further understood with reference to the following non-limiting examples.

EXAMPLE 1

Comparison of Rice Blast Fungus Extraction Versus Grinding

An extraction solution containing a dilute acid and a surfactant was used to extract rice blast fungi from rice leaves. This extraction procedure was compared with extraction of ground rice leaves with a neutral buffer.

Healthy rice leaves were inoculated with spores of *Pyricularia grisea* and collected for extraction immediately following inoculation and at 1, 2, 3, 4, 5 and 6 days after inoculation. Rice leaves that had not been inoculated were used as a negative control. Rice leaf samples were collected and stored frozen until extracted.

Rice leaves were combined with an extraction solution containing 0.01M HCl and 0.1% Poly-Tergent SLF-18™ surfactant (Olin Corporation, Stamford, Conn.)) in a plastic bottle and shaken for three minutes by hand at room temperature. The ratio of rice leaves to extraction solution was 100 mg/ml. The extract was added to immunoreagents in the presence of a neutralizing buffer (150 mM Hepes pH 8.3, 0.5M EDTA, 0.2% IgG, 0.05% BSA and 0.05% sodium azide), incubated five minutes, and applied to a cup assembly containing a filter. These immunoreagents were 50 μl of antibody-coated latex and 7.5 μl of antibody-alkaline phosphate conjugate, which were incubated with 542.5 μl of filtered extract. The extract was washed with 400 μl of a wash buffer contain 10 mM Tris, pH 8.0, 0.1% SLF-18™ detergent, and 0.05% sodium azide. 200 μl of 5-bromo-4-chloro-3-indolyl phosphate in 2-amino-2-methyl-1-propanol buffer with magnesium ions (BCIP, Sigma Chemical Co., St. Louis, Mo.) was added to the extract and incubated at room temperature for 10 minutes. The reaction produced a detectable colorimetric change that was measured by a reflectometer. The results are shown in FIG. 1, open squares, and demonstrate that fungal infection can be detected as early as four days after inoculation.

For the grinding experiment, 0.2 grams of rice leaves were combined with 2 ml of a buffer containing 50 mM Hepes, 0.1% SLF-18, 0.05M EDTA, 0.2% Rabbit IgG, 0.05% Sodium Azide, and 0.05% Bovine Serum Albumin (BSA) pH 8.3 The rice leaves were then crushed using a mortar and pestle, centrifuged at 2400 rpm for ten minutes, filtered with a 0.8 μm syringe filter (Gelman Science, Ann Arbor, Mich.) and combined with the immunoreagents as described above (no neutralization buffer was utilized). The results are shown in FIG. 1, closed squares. The irregular curve indicates that the grinding method, in contrast to the shaking method, exhibits a large amount of interference or variability, making it difficult to determine whether the leaf is contaminated with fungus.

A comparison of these two extraction methods demonstrates that extraction with the dilute acid and surfactant is superior to grinding extraction with a neutral buffer.

Modifications and variations of the plant fungus extraction method and kit will be obvious to those skilled in the art from the foregoing description. Such modifications and variations are intended to come within the scope of the appended claims.

We claim:

1. A method for extracting fungus from a plant comprising:

a) combining an extraction solution with tissue from the plant, wherein the extraction solution consists essentially of a dilute acid and an alkoxylated linear alcohol detergent, and b) agitating the combination, wherein the extraction solution extracts fungus from the plant and wherein the extraction solution is easily neutralized and does not degrade the fungus below a detectable level.

2. The method of claim 1 wherein the extraction solution reduces the amount of green color due to chlorophyll in the extract.

3. The method of claim 1 wherein the acid has a molarity of between approximately 1 mM and 50 mM.

4. The method of claim 1 wherein the acid is selected from the group consisting of hydrochloric acid, sulfuric acid, nitric acid and organic acids.

5. The method of claim 1 wherein the detergent has a concentration of between approximately 0.01 and 1%.

6. The method of claim 1 wherein the combination is shaken by hand for less than 30 minutes.

7. The method of claim 1 wherein the plant is selected from the group consisting of grasses, trees, shrubs, flowers, and ornamental plants.

8. The method of claim 1 wherein the plant is selected from the group consisting of rice, wheat, barley, rye, corn, and bananas.

9. The method of claim 1 wherein the plant is rice and the fungus is *Pyricularia oryzae.*

10. A kit for extraction of fungus from a plant comprising an extraction solution which consists essentially of:

a) a dilute acid which does not degrade the fungus, and b) an alkoxylated linear alcohol detergent.

11. The kit of claim 10 further comprising a reaction vessel in which the plant is reacted with the extraction solution.

12. The kit of claim 10 wherein the acid has a molarity of between approximately 1 mM and 50 mM.

13. The kit of claim 10 wherein the acid is selected from the group consisting of hydrochloric acid, sulfuric acid, nitric acid and organic acids.

14. The kit of claim 10 wherein the detergent has a concentration of between approximately 0.01 and 1%.

15. A method for deflecting a fungus infection on a plant comprising:

a) combining an extraction solution with tissue from the plant, wherein the extraction solution consists essentially of a dilute acid and an alkoxylated linear alcohol detergent and the extraction solution is easily neutralized and does not degrade the fungus below a detectable level;

b) agitating the combination;

c) separating the plant tissue from the extraction solution;

d) neutralizing the extraction solution; and e) detecting the presence or absence of fungus in the extraction solution by immunoassay.

16. The method of claim 15 wherein the acid is selected from the group consisting of hydrochloric acid, sulfuric acid, nitric acid and organic acids.

17. An extraction solution for the extraction of fungus from a plant consisting essentially of a dilute acid which does not degrade the fungus and an alkoxylated linear alcohol detergent.

* * * * *